(12) United States Patent
Tehrani et al.

(10) Patent No.: US 12,369,945 B2
(45) Date of Patent: Jul. 29, 2025

(54) DEVICE DELIVERY VIA BILIARY ACCESS DEVICE

(71) Applicant: BOSTON SCIENTIFIC SCIMED, INC., Maple Grove, MN (US)

(72) Inventors: Ramin N. Tehrani, Marlborough, MA (US); Eric Gacon, Shrewsbury, MA (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 324 days.

(21) Appl. No.: 17/974,904

(22) Filed: Oct. 27, 2022

(65) Prior Publication Data

US 2023/0135620 A1 May 4, 2023

Related U.S. Application Data

(60) Provisional application No. 63/272,845, filed on Oct. 28, 2021.

(51) Int. Cl.
*A61B 17/34* (2006.01)
*A61M 25/01* (2006.01)

(52) U.S. Cl.
CPC .. *A61B 17/3476* (2013.01); *A61B 2017/3425* (2013.01); *A61M 25/0102* (2013.01)

(58) Field of Classification Search
CPC ............ A61B 17/3476; A61B 17/3496; A61B 2017/00367; A61B 2017/3425; A61F 2/962; A61F 2/966; A61M 25/0102
See application file for complete search history.

(56) References Cited

U.S. PATENT DOCUMENTS

| | | |
|---|---|---|
| 4,580,568 A | 4/1986 | Gianturco |
| 4,830,003 A | 5/1989 | Wolff et al. |
| 5,484,444 A | 1/1996 | Braunschweiler et al. |
| 5,876,448 A | 3/1999 | Thompson et al. |

(Continued)

FOREIGN PATENT DOCUMENTS

| | | |
|---|---|---|
| EP | 1690512 A1 | 8/2006 |
| EP | 3808316 A1 | 4/2021 |

OTHER PUBLICATIONS

International Search Report and Written Opinion dated May 30, 2023 for International Application No. PCT/US2022/048020.

(Continued)

*Primary Examiner* — Todd J Scherbel
(74) *Attorney, Agent, or Firm* — Seager, Tufte & Wickhem, LLP

(57) ABSTRACT

A delivery endcap assembly is adapted for use with a biliary access device and is adapted to permit a medical device to be delivered through the biliary access device. The delivery endcap assembly includes a securement portion adapted to be releasably securable to a proximal end of the handle after the one or more removable components have been removed from the handle, a tapered portion extending proximally from the securement portion, a rotation hub adapted to be coupled to the securement portion, a valve adapted to be coupled to the rotation hub and a lumen extending through the delivery endcap assembly, wherein the lumen extending through the delivery endcap assembly is adapted to permit a medical device within an introducer sheath to be advanced through the biliary access device.

16 Claims, 22 Drawing Sheets

(56) References Cited

U.S. PATENT DOCUMENTS

| | | |
|---|---|---|
| 6,911,040 B2 | 6/2005 | Johnson et al. |
| 7,468,070 B2 | 12/2008 | Henry et al. |
| 8,821,565 B2 | 9/2014 | Demetriades et al. |
| 9,393,137 B2 | 7/2016 | Rusk et al. |
| 9,974,561 B2 | 5/2018 | Benning et al. |
| 10,821,008 B2 | 11/2020 | Gorochow |
| 2002/0013599 A1 | 1/2002 | Limon et al. |
| 2007/0270931 A1 | 11/2007 | Leanna et al. |
| 2007/0270932 A1 | 11/2007 | Headley et al. |
| 2007/0270937 A1 | 11/2007 | Leanna |
| 2012/0226341 A1* | 9/2012 | Schreck .................. A61F 2/07 623/1.11 |
| 2015/0374522 A1 | 12/2015 | Wood et al. |
| 2016/0235561 A1 | 8/2016 | Wrobel et al. |
| 2016/0361088 A1 | 12/2016 | Maguire et al. |
| 2018/0256200 A1 | 9/2018 | Benning et al. |
| 2020/0345212 A1 | 11/2020 | Dreyer et al. |
| 2021/0030460 A1 | 2/2021 | Mayo et al. |
| 2021/0128873 A1 | 5/2021 | Scott et al. |
| 2021/0186607 A1 | 6/2021 | Scott et al. |
| 2021/0236105 A1 | 8/2021 | Hansen et al. |
| 2021/0282807 A1 | 9/2021 | Tehrani et al. |

OTHER PUBLICATIONS

Invitation to Pay Additional Fees dated Feb. 27, 2023 for International Application No. PCT/US2022/048020.

\* cited by examiner

DEVICE DELIVERY VIA BILIARY ACCESS DEVICE

CROSS-REFERENCE TO RELATED APPLICATIONS

This application claims the benefit of U.S. Provisional Patent Application Ser. No. 63/272,845, filed Oct. 28, 2021, which is incorporated herein by reference.

TECHNICAL FIELD

The present disclosure pertains to medical devices, and methods for manufacturing and using medical devices. More particularly, the disclosure is directed to using a biliary access device to subsequently deliver a medical device such as an expandable stent.

BACKGROUND

A wide variety of medical devices have been developed for medical use, for example, for use in accessing body cavities and interacting with fluids and structures in body cavities. Some of these devices may include guidewires, catheters, pumps, motors, controllers, filters, grinders, needles, valves, and delivery devices and/or systems used for delivering such devices. These devices are manufactured by any one of a variety of different manufacturing methods and may be used according to any one of a variety of methods. Of the known medical devices and methods, each has certain advantages and disadvantages.

SUMMARY

This disclosure provides design, material, manufacturing method, and use alternatives for medical devices. As an example, an assembly for deploying a medical device within a biliary or pancreatic duct of a patient includes a biliary access device and a delivery endcap assembly. The biliary access device includes a handle and an electrosurgical sheath that is movable relative to the handle, the electrosurgical sheath including an electrosurgical tip and defining an electrosurgical sheath lumen extending through the electrosurgical sheath. An access cannula is extendable through the electrosurgical sheath lumen and defines a cannula lumen extending through the access cannula, the access cannula adapted to be removable from the biliary access device. A sharp stylet is extendable through the cannula lumen and is adapted to be removable from the biliary access device. An access endcap assembly is disposable at a proximal end of the handle and is adapted to be removable from the biliary access device. The delivery endcap assembly is adapted to be securable to the proximal end of the handle in place of the access endcap assembly. The delivery endcap assembly includes a securement portion that is adapted to be releasably securable to the proximal end of the handle, and a lumen that extends through the delivery endcap assembly and is adapted to accommodate the medical device therethrough.

Alternatively or additionally, the delivery endcap assembly may further include a tapered portion extending proximally from the securement portion, a rotation hub adapted to be coupled to the securement portion, and a valve adapted to be coupled to the rotation hub, where the lumen of the delivery endcap assembly extends through each of the tapered portion, the rotation hub and the valve.

Alternatively or additionally, the access endcap assembly may further include a rotation hub.

Alternatively or additionally, the sharp stylet may further include a sharp cap that is adapted to releasably secure the sharp stylet to the rotation hub.

Alternatively or additionally, the access cannula may be operably coupled with the rotation hub such that rotation of the rotation hub causes rotation of the access cannula.

Alternatively or additionally, the access cannula may be operably coupled with the rotation hub such that removal of the rotation hub also removes the access cannula from the biliary access device.

Alternatively or additionally, the lumen of the delivery endcap assembly may be positionable in alignment and in communication with the electrosurgical sheath lumen such that the electrosurgical sheath is adapted to accommodate the medical device extending through the electrosurgical sheath lumen once the access cannula and the sharp stylet have been removed from the biliary access device and the delivery endcap assembly has been secured to the proximal end of the handle of the biliary access device.

Alternatively or additionally, the medical device may include an expandable stent disposed within an introducer sheath.

Alternatively or additionally, the introducer sheath may be adapted to engage a proximal end of the electrosurgical sheath lumen such that a mandrel may be used to advance the expandable stent from the introducer sheath through the electrosurgical sheath lumen.

Alternatively or additionally, the handle may include an inner member and an outer member, the inner member slidingly disposed within the outer member, and translating the inner member relative to the outer member may cause the sharp stylet to translate.

Alternatively or additionally, the handle may further include an electrosurgical actuator slidingly coupled with the outer member of the handle, and translating the electrosurgical actuator relative to the handle may cause the electrosurgical sheath to translate.

Alternatively or additionally, the delivery endcap assembly may further include a modified rotation hub.

As another example, a delivery endcap assembly is adapted for use with a biliary access device that is adapted for providing access to a treatment site, the biliary access device including a handle, a sheath extending proximally from the handle and one or more removable components extending proximally within the sheath, the one or more removable components adapted for providing access, the delivery endcap assembly adapted to permit a medical device to be delivered through the biliary access device. The delivery endcap assembly includes a securement portion adapted to be releasably securable to a proximal end of the handle after the one or more removable components have been removed from the handle. A tapered portion extends proximally from the securement portion and a rotation hub is adapted to be coupled to the securement portion. A valve is adapted to be coupled to the rotation hub. A lumen extends through the delivery endcap assembly and is adapted to permit a medical device within an introducer sheath to be advanced through the biliary access device.

Alternatively or additionally, one of the one or more removable components may include a sharp stylet operably coupled with a sharp stylet cap removably securable to the biliary access device.

Alternatively or additionally, one of the one or more removable components may include an access cannula operably coupled with a rotation hub removably securable to the biliary access device.

Alternatively or additionally, the medical device may include an expandable stent disposed within an introducer sheath, the introducer sheath adapted to butt up against a proximal end of the sheath such that a mandrel may be used to advance the expandable stent through the biliary access device.

In another example, a medical device is delivered using a biliary access device adapted to provide an access aperture providing access to a desired site within the patient's anatomy, the access device including a handle and a stylet distally extendable from the handle within a sheath. The access device is used to reach the desired site within the patient's anatomy and the stylet is extended to provide a puncture at the desired site, the puncture forming the access aperture. The stylet is withdrawn from the sheath and the handle. A delivery endcap assembly is attached to the handle, the delivery endcap assembly adapted to provide access to a lumen extending through the sheath. A guidewire is extended through the access device and through the access aperture. The medical device is extended through the delivery endcap assembly and down the guidewire to the desired site. The medical device is deployed at the desired site.

Alternatively or additionally, the sheath may include an electrosurgical sheath with an electrosurgical tip disposed at a distal end of the electrosurgical sheath, and the method may further include using the electrosurgical tip to enlarge the access aperture formed by the stylet.

Alternatively or additionally, the medical device may include an expandable stent disposed within an introducer sheath, the introducer sheath adapted to butt up against a proximal end of the electrosurgical sheath such that a mandrel may be used to advance the expandable stent through the biliary access device.

Alternatively or additionally, the delivery endcap assembly may include a securement portion adapted to be releasably securable to a proximal end of the handle after the stylet has been removed from the handle, a tapered portion extending proximally from the securement portion, a rotation hub adapted to be coupled to the securement portion, a valve adapted to be coupled to the rotation hub, and a lumen extending through the delivery endcap assembly, where the lumen extending through the delivery endcap assembly is adapted to permit a medical device within an introducer sheath to be advanced through the biliary access device.

The above summary of some embodiments is not intended to describe each disclosed embodiment or every implementation of the present disclosure. The Figures, and Detailed Description, which follow, more particularly exemplify these embodiments.

BRIEF DESCRIPTION OF THE DRAWINGS

The invention may be more completely understood in consideration of the following detailed description of various embodiments of the invention in connection with the accompanying drawings, in which.

Figure 1A:
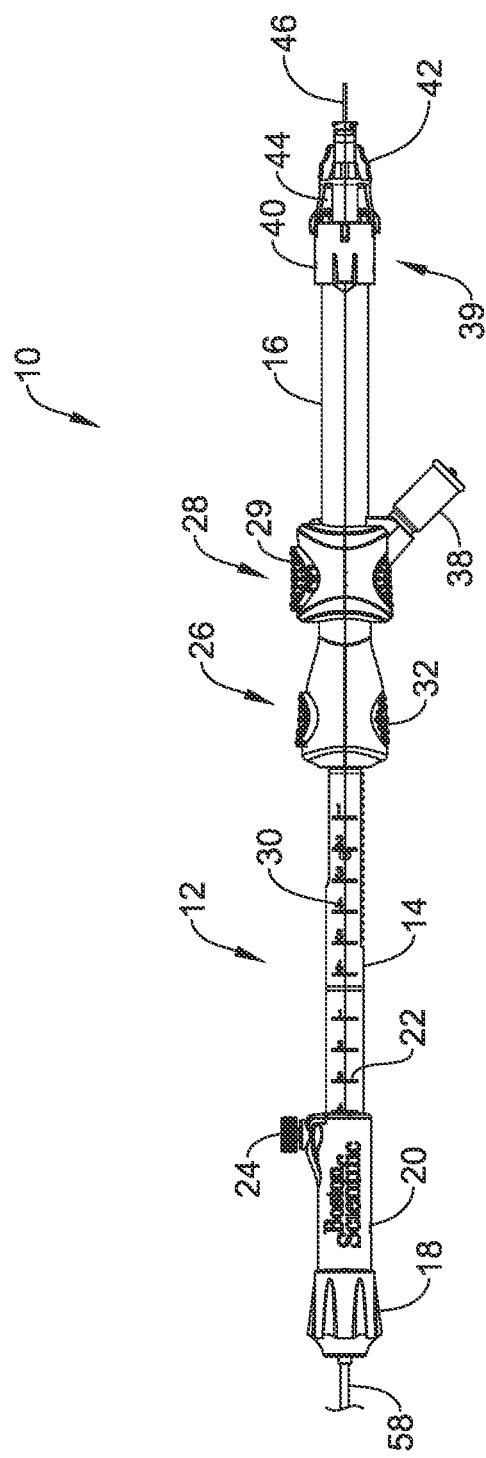
FIG. 1A is a side view of an illustrative biliary access device.

While the disclosure is amenable to various modifications and alternative forms, specifics thereof have been shown by way of example in the drawings and will be described in detail. It should be understood, however, that the intention is not to limit the disclosure to the particular embodiments described. On the contrary, the intention is to cover all modifications, equivalents, and alternatives falling within the spirit and scope of the disclosure.

DESCRIPTION

For the following defined terms, these definitions shall be applied, unless a different definition is given in the claims or elsewhere in this specification.

All numeric values are herein assumed to be modified by the term "about," whether or not explicitly indicated. The term "about" generally refers to a range of numbers that one of skill in the art would consider equivalent to the recited value (i.e., having the same function or result). In many instances, the terms "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

The following detailed description should be read with reference to the drawings in which similar elements in different drawings are numbered the same. The drawings, which are not necessarily to scale, depict illustrative embodiments and are not intended to limit the scope of the invention.

Figure 1B:
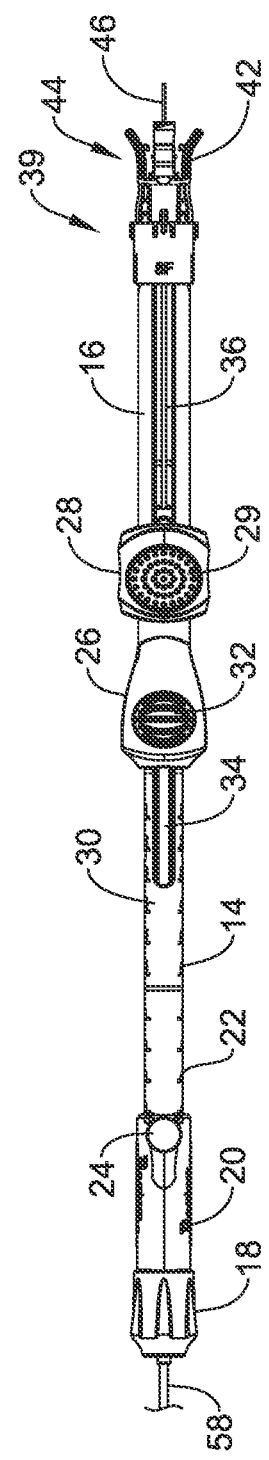
FIG. 1B is a top view of the illustrative biliary access device of FIG. 1A.

FIG. 1A is a side view of an illustrative biliary access device 10 and FIG. 1B is a top view thereof. While the disclosure concentrates on gaining access and ultimately delivering a medical device as a biliary access device 10, it will be appreciated that this is merely illustrative, as the concepts described herein are equally applicable to gaining access and ultimately delivery a medical device to any of a variety of different regions or systems of the human anatomy.

The illustrative biliary access device 10 may be used to access the biliary and pancreatic ducts as well as pancreatic pseudocysts through an accessory channel of an ultrasound endoscope. The biliary access device 10 facilitates guidewire placement for rendezvous procedures and for placement of ancillary devices such as stents that are delivered over the guidewire. The biliary access device 10 provides the ability to puncture a target site through the patient's stomach or duodenum, advance and direct a guidewire to the target site, and to dilate the fistula. The biliary access device 10 may be used under endoscopic ultrasound (EUS) guidance, fluoroscopy or even direct visualization.

The illustrative biliary access device 10 includes handle 12 that includes an inner member 14 and an outer member 16. The inner member 14 may be slidingly disposed within and extend distal of the outer member 16, for example. The handle 12 includes a nut 18 by which the biliary access device 10 may be secured to an accessory or other channel of an endoscope. A length adjustment mechanism 20 is coupled with the nut 18 and can be used to adjust the relative length of the biliary access device 10. In some cases, a scale 22 is disposed along the inner member 14 and can be used as a guide in adjusting the relative length of the biliary access device 10. The length adjustment mechanism 20 includes a securement feature 24 that may be used to secure the length adjustment mechanism 20 in place against the inner member 14, and thus adjust the relative length of the biliary access device 10.

The biliary access device 10 includes a first actuation member 26 and a second actuation member 28. In some cases, the first actuation member 26 may be secured to a distal end of the outer member 16 and may be actuated to move the outer member 16 relative to the inner member 14 and thus cause the outer member 16 to translate longitudinally relative to the inner member 14. A scale 30 may be disposed on the inner member 14 as a guide to moving the outer member 16 relative to the inner member 14.

It will be appreciated that by using the scale 30 in combination with the first actuation member 26, an operator may control axial translation of the outer member 16 relative to the inner member 14, and hence control longitudinal translation of any internal members that are secured relative to the outer member 16. Accordingly, the operator can cause one or more internal members to translate a particular distance, as indicated by the scale 30. The first actuation member 26 includes an actuation button 32 that may be depressed in order to move the first actuation member 26 relative to the inner member 14. As can be seen in FIG. 1B, the inner member 14 includes a slot 34 that allows the first actuation member 26 and thus the outer member 16 to translate longitudinally relative to the inner member 14.

The second actuation member 28 is adapted to translate relative to the outer member 16, as facilitated by the slot 36 seen in FIG. 1B. The second actuation member 28 includes an actuation button 29 that may be used to move the second actuation member 28 relative to the outer member 16. In some cases, the second actuation member 28 may be operably coupled with an electrosurgical element, and thus the second actuation member 28 may include an electrical connection 38 by which the electrosurgical element may be powered.

The biliary access device 10 includes several components at a proximal end 39 that provide functionality for the biliary access device 10 in providing access to a desired site, and that can be removed from the biliary access device 10 in order to allow a medical device to be delivered through the biliary access device 10. The biliary access device 10 includes an end cap 40, a sharp cap 42 and a rotation hub 44 that is partially visible underneath the sharp cap 42.

Figure 1C:
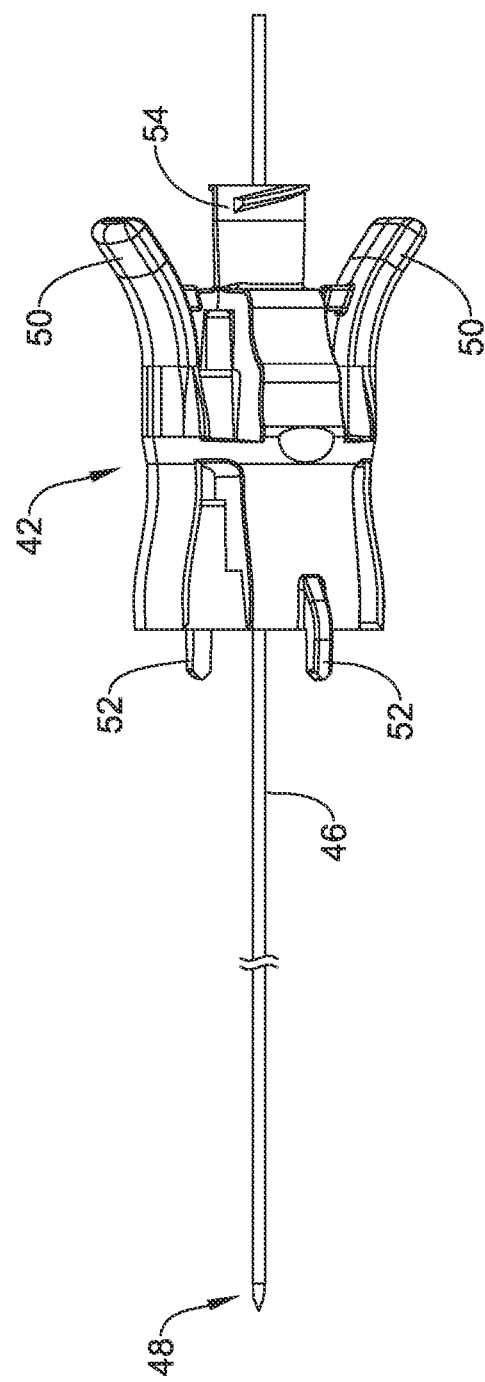
FIG. 1C is a side view of a portion of the illustrative biliary access device of FIGS. 1A and 1B.

With reference to FIG. 1C, the sharp cap 42 is operably coupled with a sharp stylet 46. For instance, a proximal end region of the sharp stylet 46 may be fixedly secured to the sharp cap 42 and extend distally therefrom. The sharp stylet 46 includes a sharp distal tip 48 that may be used to form a puncture in tissue by moving the outer member 16 distally relative to the inner member 14 to expose the sharp distal tip 48 at a distal end of the device 10. The sharp cap 42 may fit over the rotation hub 44 and may be releasably securable to the end cap 40. Accordingly, the sharp cap 42 includes grasping features 50 that may be used to remove the sharp cap 42 (and hence the sharp stylet 46) from the endcap 40. The sharp cap 42 also includes securement features 52 (e.g., distally extending tabs) that may be used to releasably secure the sharp cap 42 to the endcap 40. In some cases, as illustrated, the sharp cap 42 may include a luer fitting 54 that may be used to attach additional elements to the sharp cap 42.

Figure 1D:
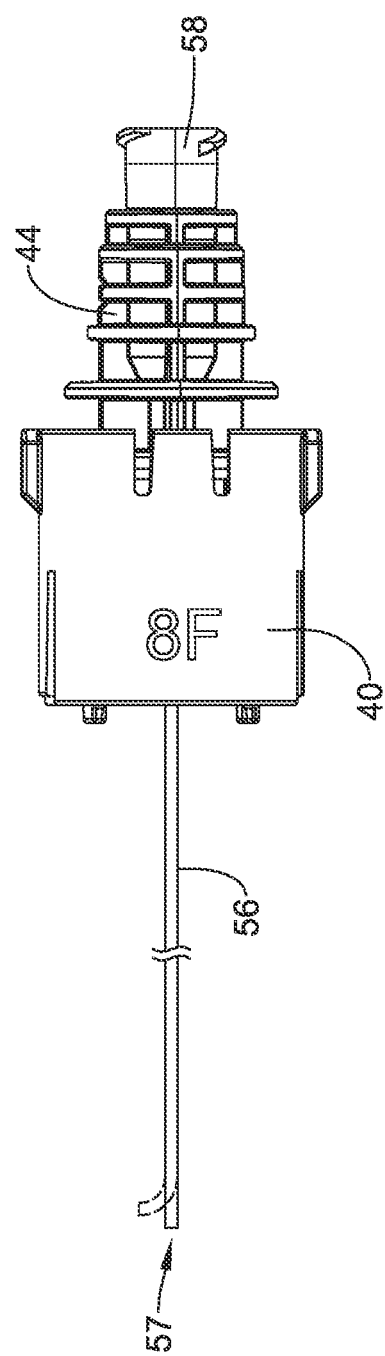
FIG. 1D is a side view of a portion of the illustrative biliary access device of FIGS. 1A and 1B.

With reference to FIG. 1D, an access cannula 56 extends distally from the endcap 40 and the rotation hub 44. The access cannula 56 defines a cannula lumen 57 extending through the access cannula 56. The cannula lumen 57 may extend through the entire length of the access cannula 56 such that the cannula lumen 57 opens out to a luer fitting 58 at a proximal end. In some instances, the cannula lumen 57 may be dimensioned to accommodate the sharp stylet 46 extending therethrough. In some cases, a distal region of the access cannula 56 may have a particular shape in order to facilitate accessing tortuous portions of the patient's anatomy. For example, a distal region of the access cannula 56 may have a J-shape (shown in dashed lines) when the sharp stylet 46 has been withdrawn from the distal region of the access cannula 56, whereas the sharp stylet may straighten the J-shape tip of the access cannula 56 when inserted therein. By rotating the access cannula 56, and by virtue of the shaped distal region, an operator can steer the access cannula 56 into a particular duct or branch of a duct, for example. The rotation hub 44 includes a luer fitting 58 that can be used to attach additional elements to the rotation hub 44 when the sharp cap 42 has been removed or it otherwise not present. Other attachment techniques are also contemplated.

Figure 1E:
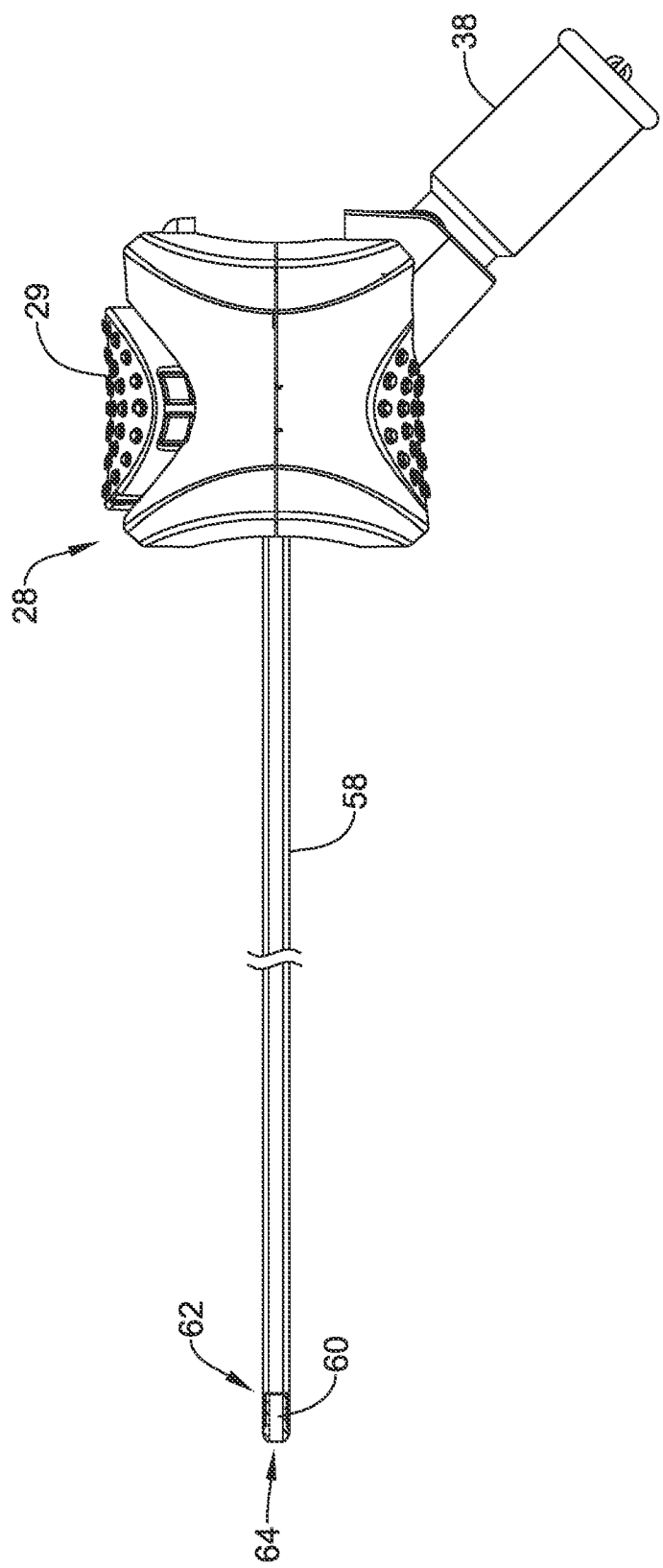
FIG. 1E is a side view of a portion of the illustrative biliary access device of FIGS. 1A and 1B.

With reference to FIG. 1E, an electrosurgical sheath 58 extends distally from the second actuation member 28. The electrosurgical sheath 58 includes an electrosurgical tip 60 that is disposed at a distal end 62 of the electrosurgical sheath 58. An electrosurgical sheath lumen 64 extends through the electrosurgical sheath 58. In some instances, the electrosurgical sheath lumen 64 may be dimensioned to accommodate the access cannula 56 extending therethrough. In some cases, the electrosurgical sheath lumen 64 also extends through the electrosurgical tip 60 to a distalmost extent of the electrosurgical sheath 58. It will be appreciated, therefore, that the electrosurgical sheath lumen 64 provides a path for delivering and deploying a medical device that can be advanced through the electrosurgical sheath lumen 64 once particular elements have been removed from the biliary access device 10.

Additional details regarding the internal structure of the illustrative biliary access device 10 may be found in US 2021/0282807, filed Feb. 18, 2021 and entitled DEVICE, A SYSTEM, AND A METHOD FOR ACCESS CANNULA ADVANCEMENT; and US 2021/0236105, filed Feb. 2, 2021 entitled MEDICAL DEVICE ROTATION ASSEMBLIES AND METHODS OF USING THE SAME, which applications are incorporated by reference herein in their entirety.

Figure 2:
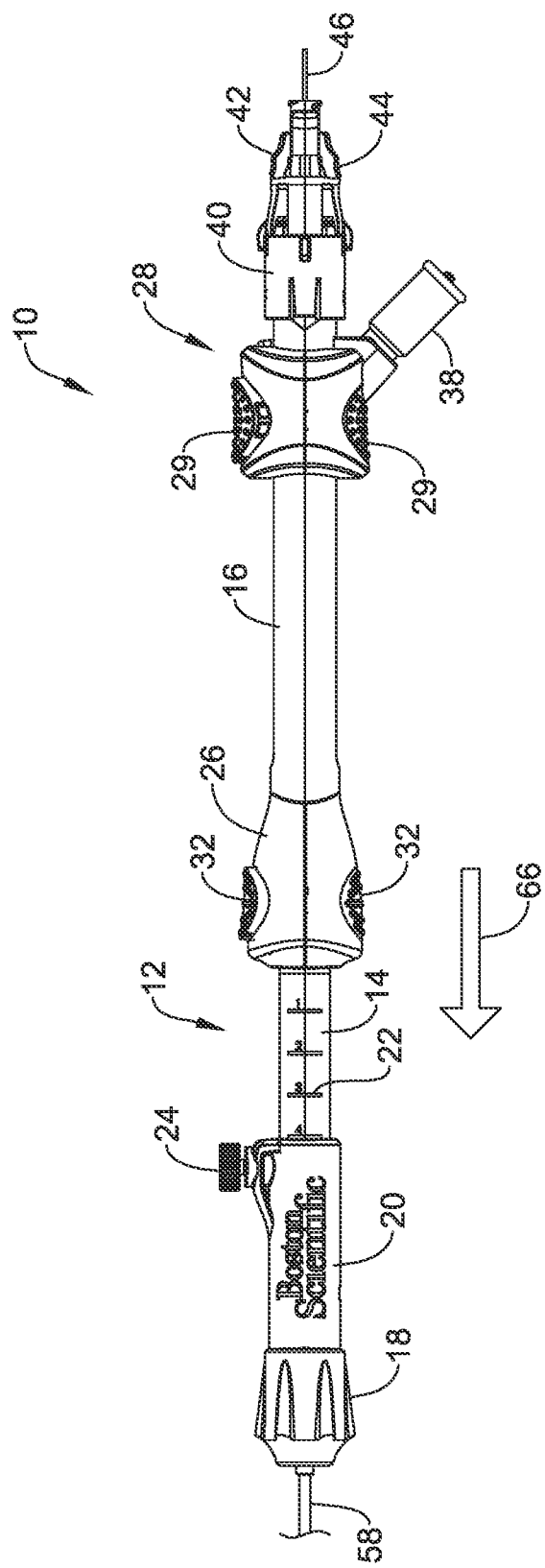
FIGS. 2 through 5 show a method of using the illustrative biliary access device of FIGS. 1A and 1B to provide access.

FIGS. 1A and 1B show the illustrative biliary access device 10 in a home position. In FIG. 2, the first actuation member 26 has been moved distally in a direction indicated by an arrow 66 by actuating the actuation button 32. As a result, the sharp stylet 46 is moved distally a sufficient distance be exposed from the distal end of the access cannula 56 and beyond the electrosurgical sheath 58 and to contact tissue in which a puncture is desired. The sharp distal tip 48 of the sharp stylet 46 will penetrate the tissue and form a puncture.

Figure 3:
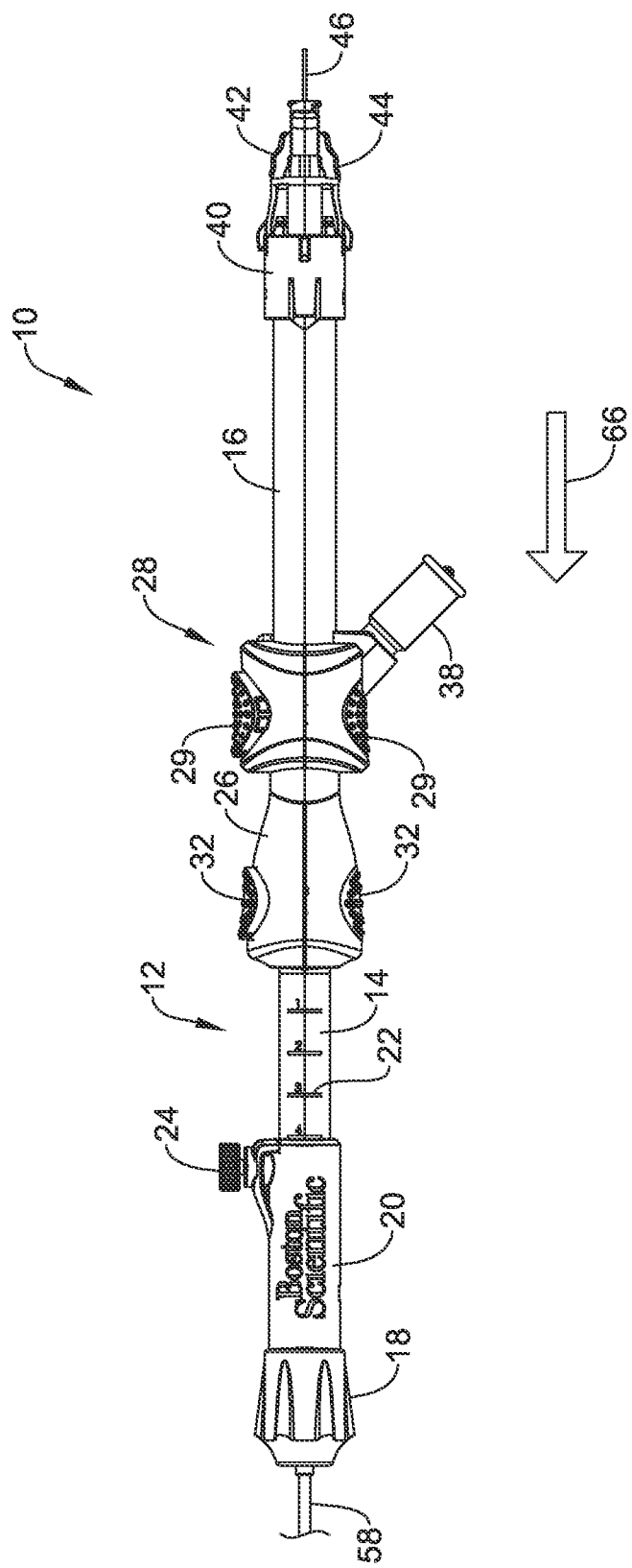
Figure 4:
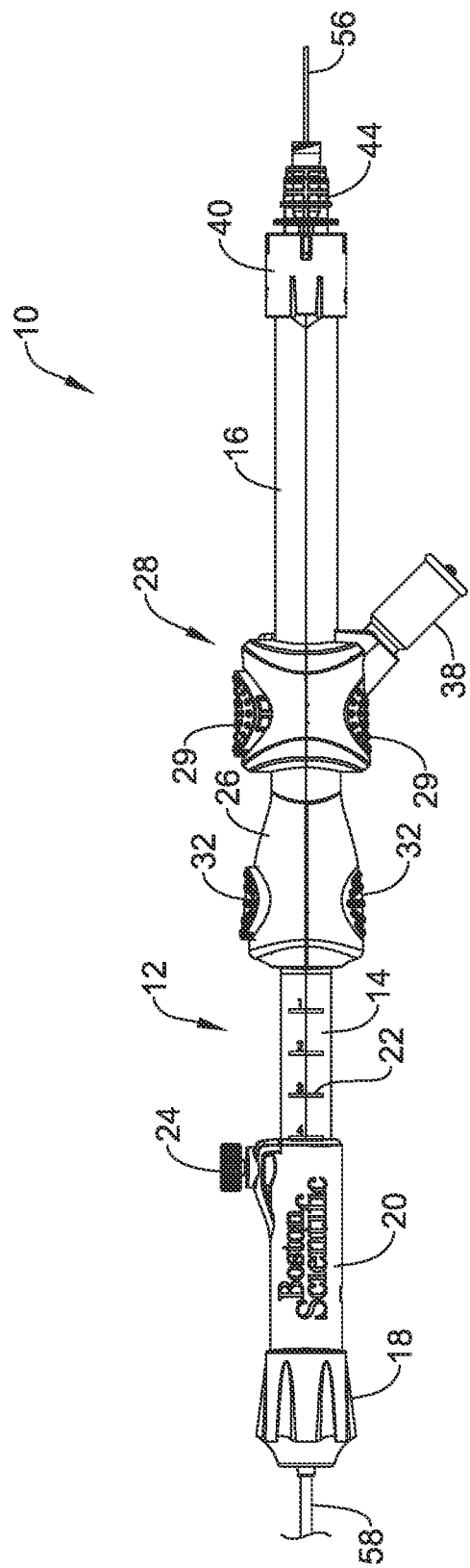

In FIG. 3, the second actuation member 28 has been moved distally in a direction indicated by an arrow 68 by actuating the actuation button 29. As a result, the electrosurgical sheath 58 is moved distally relative to the access cannula 56 and the sharp stylet 46 such that the electrosurgical tip 60 is brought into contact with the puncture. The sharp cap 42 and the sharp stylet 46 may be removed from the biliary access device 10, as shown in FIG. 4 by withdrawing the sharp stylet 46 proximally from the handle 12. The electrosurgical tip 60 may then be actuated in order to create a larger aperture where the puncture was originally created by the sharp distal tip 48 of the sharp stylet 46. In some cases, the electrosurgical tip 60 may be used to enlarge the opening to be an 8F (French) opening. In some cases, the opening may be referred to as a fistula, which refers to an opening between two bodily structures that do not normally have an opening therebetween.

Figure 5:
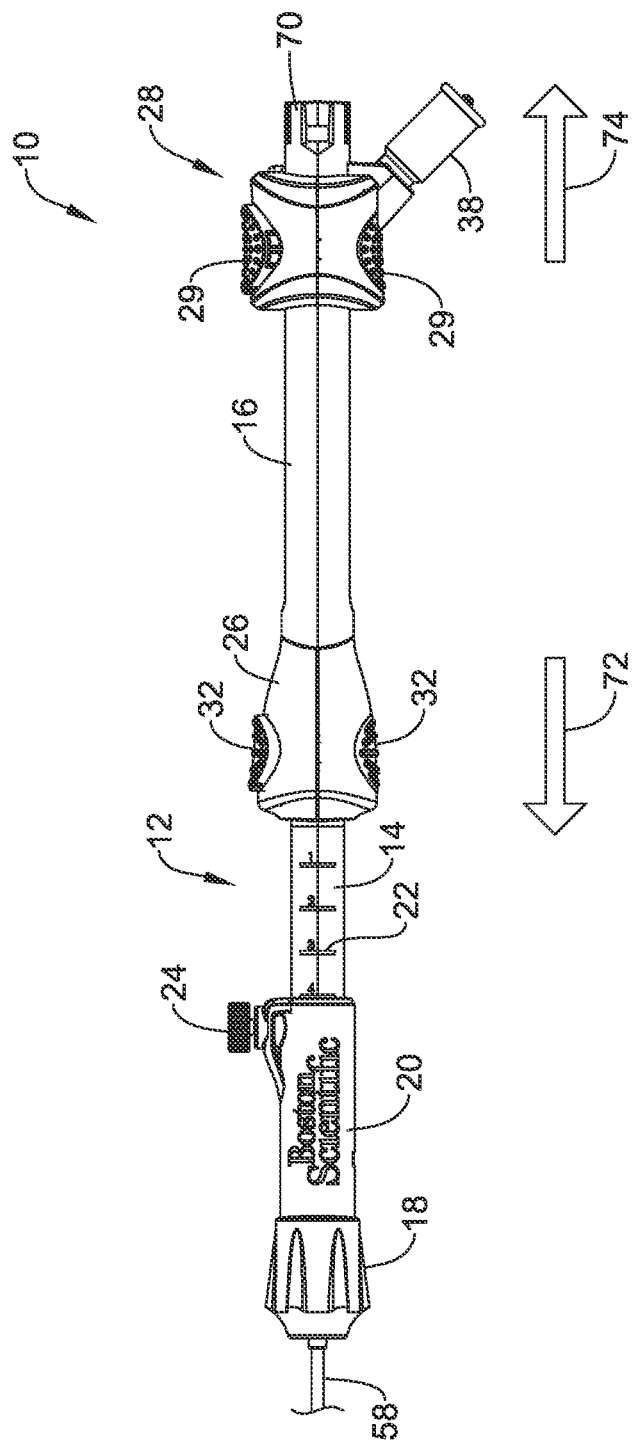

Next, the rotation hub 44 and attached access cannula 56 are removed from the biliary access device 10. The endcap 40 is also removed. The sharp cap 42 and the sharp stylet 46 were previously removed. FIG. 5 illustrates the biliary access device 10 with these elements removed. The handle 12 includes a proximal end 70 that is adapted to releasably secure the endcap 40 thereto, with the rotating hub 44 and the sharp cap 42 adapted to be secured to the endcap 40. As will be discussed, additional elements may be secured to the proximal end 70 in order to now use the biliary access device 10 for delivering a medical device.

To prepare the biliary access device 10 to be used to deliver a medical device, and with reference to FIG. 5, the first actuation member 26 is moved in a direction indicated by an arrow 72 (i.e., distally) to a full throw position and the second actuation member 28 is moved in a direction indicated by an arrow 74 (i.e., proximally) to a home position. In other words, the first actuation member 26 and the second actuation member 28 may be moved in opposition directions. This allows attachment of additional elements for delivery.

Figure 6A:
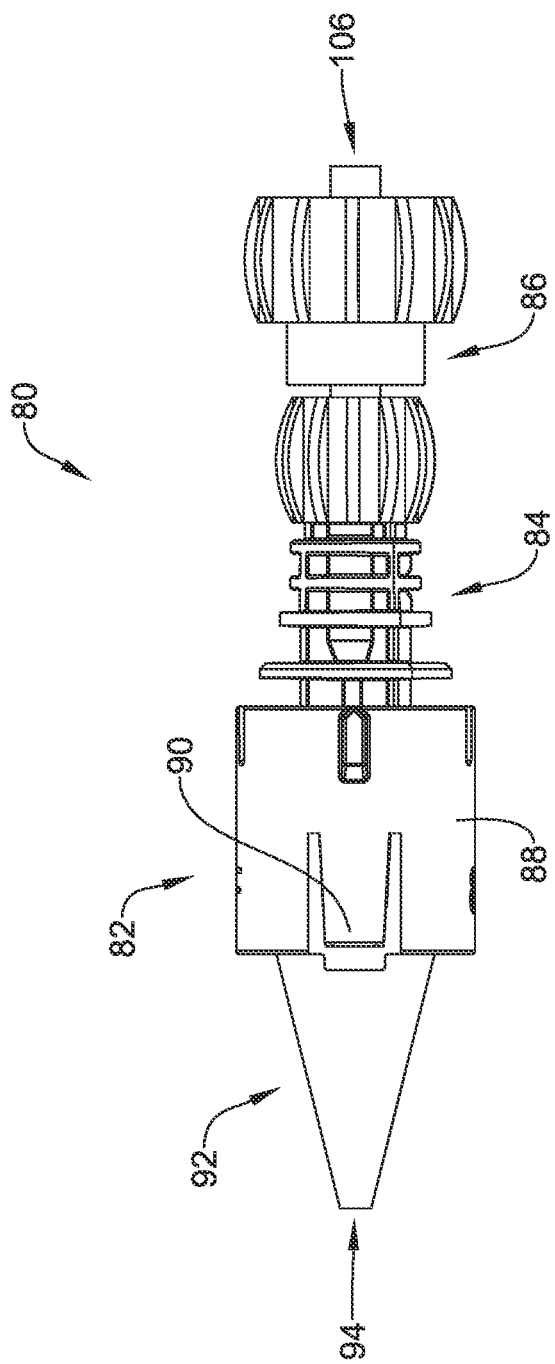
FIG. 6A is a side view of an illustrative delivery endcap assembly usable with the illustrative biliary access device of FIGS. 1A and 1B for delivering a medical device.
Figure 6B:
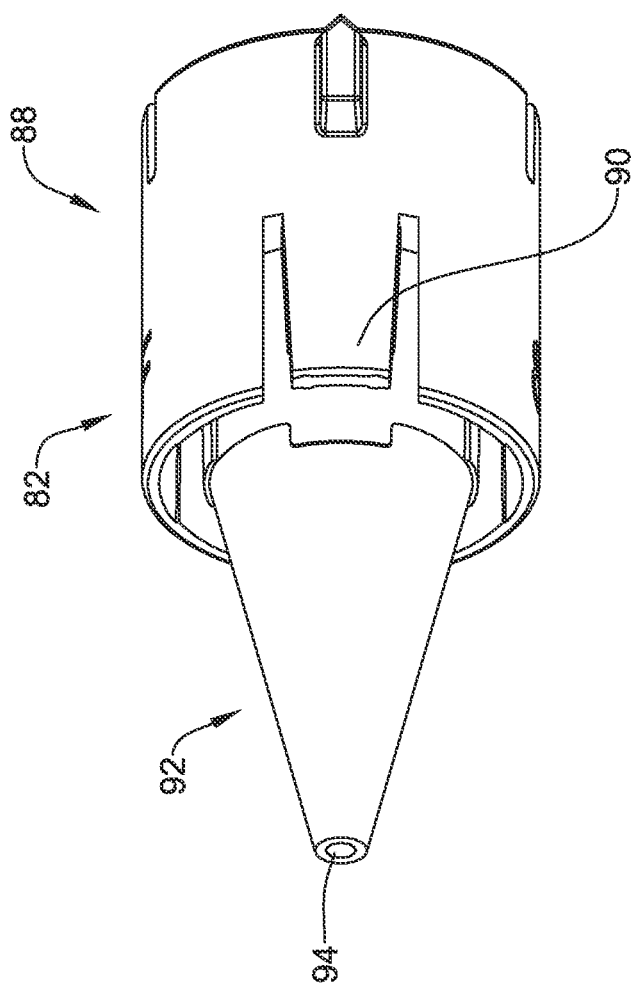
FIGS. 6B through 6E are perspective views of portions of the illustrative delivery endcap assembly of FIG. 6A.

FIG. 6A is a side view of a delivery endcap assembly 80. The delivery endcap assembly 80 is adapted to be securable to the proximal end 70 of the handle 12 (with the access endcap 40 removed) in order to facilitate use of the biliary access device 10 in subsequently delivering a medical device through a fistula created by the biliary access device 10 at an anatomical location reached by the biliary access device 10. The delivery endcap assembly 80 may include a delivery endcap 82, a delivery rotation hub 84 and/or a delivery valve 86. FIG. 6B is a perspective view of the delivery endcap 82. In some cases, the delivery valve 86 is a Touhy Borst adaptor that enables devices to be extended into and through the delivery valve 86 without allowing fluid such as various bodily fluids or saline from leaking out around whatever device is being extended through the delivery valve 86.

The delivery endcap 82 may be considered as including a securement portion 88 that may be adapted to be releasably secured to the proximal end 70 of the handle 12. In some cases, the securement portion 88 includes one or more latches 90 that are adapted to interact with the proximal end 70 of the handle 12 in order to secure the securement portion 88 to the proximal end 70 of the handle 70. While shown as being several latches 90 (there is another latch 180 degrees about the circumference of the securement portion 88 from the visible latch 90), in some cases other securement techniques may be used. For example, the securement portion 88 may form a frictional fit with the proximal end 70 of the handle 12. The securement portion 88 may be adapted to be threadedly engaged with the proximal end 70 of the handle 12. The securement portion 88 may be snap fit into engagement with the proximal end 70 of the handle 12. These are just examples.

Figure 6C:
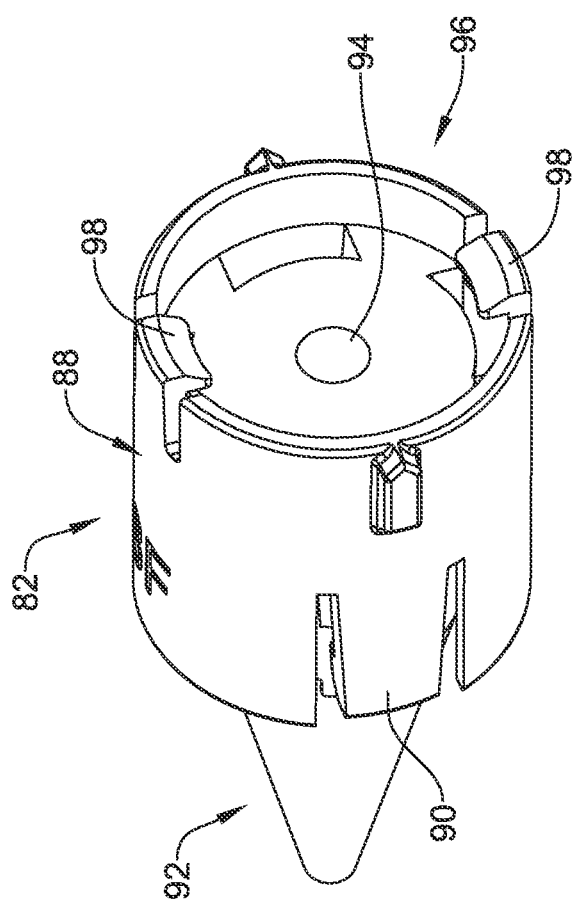

FIG. 6B is a first perspective view of the delivery endcap 82 highlighting a tapered portion 92 extending distally while FIG. 6C is a second perspective view of the delivery endcap 82 highlighting an opposing proximal end 96. The delivery endcap 82 includes a lumen 94 that extends longitudinally through the delivery endcap 82 from the proximal end to the distal end of the delivery endcap 82. The opposing proximal end 96 may include one or more latches, such as a pair of latches 98 that are adapted to engage the rotation hub 84. Other securement techniques are also contemplated.

The tapered portion 92 may be frustoconical, and may include an outer wall tapering to a smaller diameter in a distal direction to or toward the distal end of the tapered portion 92 and/or an inner wall (defining a lumen therethrough) tapering to a smaller diameter in a distal direction to or toward the distal end of the tapered portion 92. As will be discussed, the tapered portion 92 is adapted to engage a sheath extending within the biliary access device 10 in order to provide a contiguous lumen extending therethrough. In some cases, the sheath extending through the biliary access device 10 may be the electrosurgical sheath 58. In some cases, another sheath or hypotube may extend between the electrosurgical sheath 58 and the tapered portion 92 and the lumen 94 extending therethrough. Thus, the lumen through the delivery endcap 82 (including through the tapered portion 92) may be placed in alignment and communication with the lumen of the sheath, such as the lumen of the electrosurgical sheath 58.

Figure 6D:
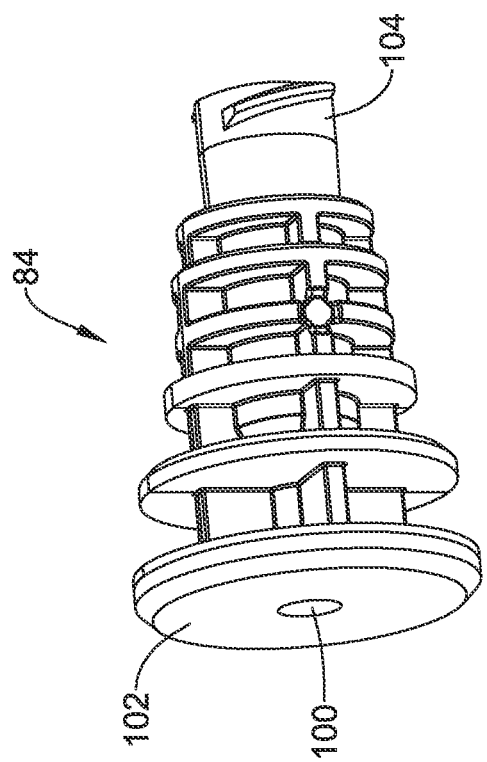

The delivery rotation hub 84 is adapted to engage the latches 98 in order to secure the rotation hub 84 to the delivery endcap 82. FIG. 6D is a perspective view of the delivery rotation hub 84. The delivery rotation hub 84 includes a lumen 100 that extends through the delivery rotation hub 84. The lumen 100 is aligned with and in communication with the lumen 94 of the tapered portion 92. The delivery rotation hub 84 includes an annular engagement section 102 that is adapted to seat into the end 96 of the delivery endcap 82 and be held in place there via the latches 98. Other securement mechanisms that fixedly attach or rotationally attach the delivery rotation hub 84 to the delivery endcap 82 are also contemplated. The delivery rotation hub 84 may include a luer fitting 104 that may be used to couple other devices to the delivery rotation hub 84, such as but not limited to the delivery valve 86.

Figure 6E:
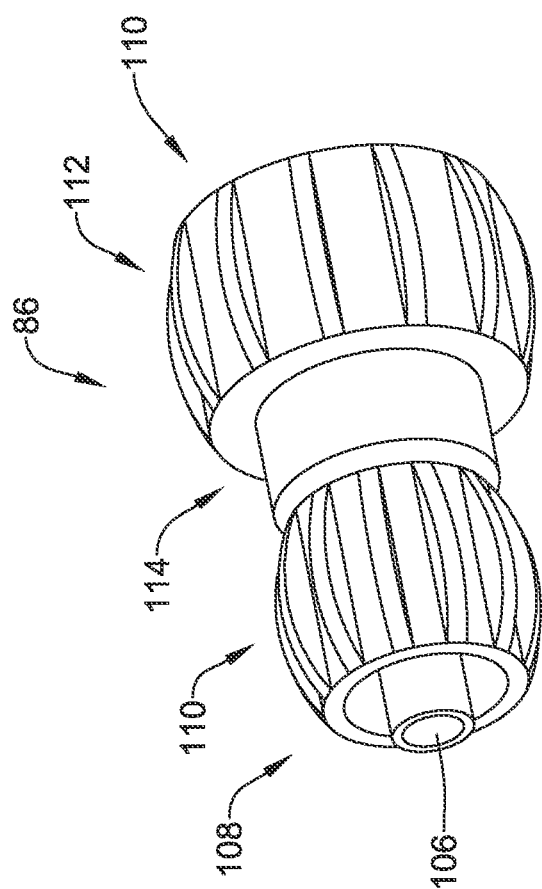

FIG. 6E is a perspective view of the delivery valve 86. As noted, in some cases, the delivery valve 86 may be a Touhy Borst adaptor. The delivery valve 86 includes a lumen 106 that extends through the delivery valve 86. The lumen 106 is aligned with and in communication with both the lumen 100 of the delivery rotation hub 84 and the lumen 94 of the tapered portion 92. Accordingly, a medical device can be advanced through the lumen 106 of the delivery valve 86, then through the lumen 100 of the delivery rotation hub 84, then through the lumen 94 of the tapered portion 92 of the delivery endcap 82 and into the lumen of the sheath extending therefrom, such that the medical device can be delivered through the sheath and deployed out from the sheath to a treatment site. The delivery valve 86 includes a first region 108 that is adapted to be secured relative to the delivery rotation hub 84. In some cases, the first region 108 frictionally engages the luer fitting 104 in place on the delivery rotation hub 84. The delivery valve 86 includes a first knurled portion 110 and a second knurled portion 112, divided by a cylindrical portion 114.

Figure 7:
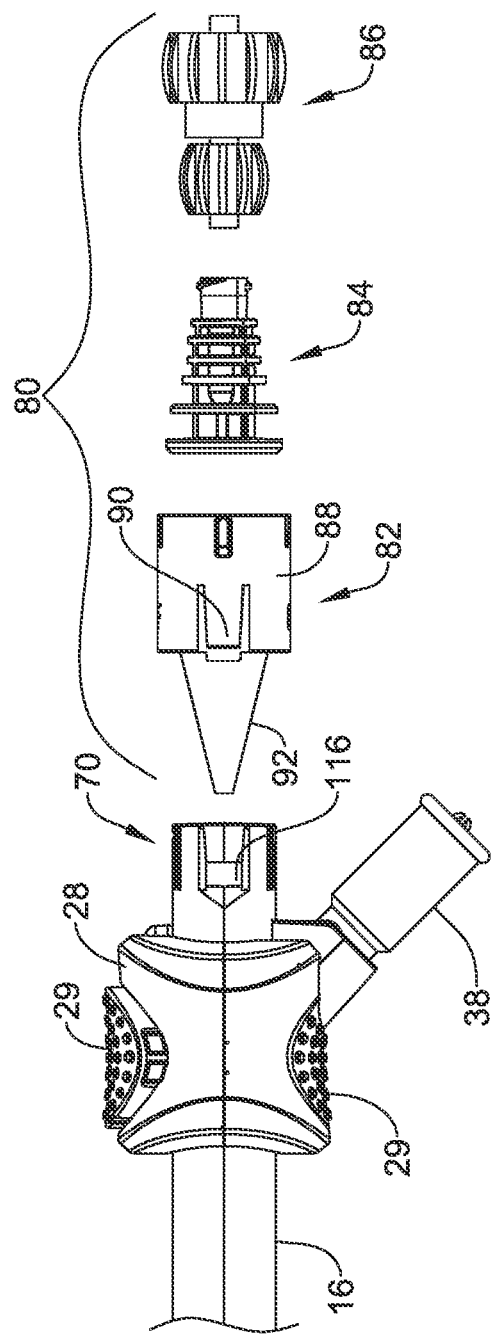
FIG. 7 is a partial exploded side view of the illustrative delivery endcap assembly of FIG. 6A in combination with the illustrative biliary access device of FIGS. 1A and 1B.
Figure 8:
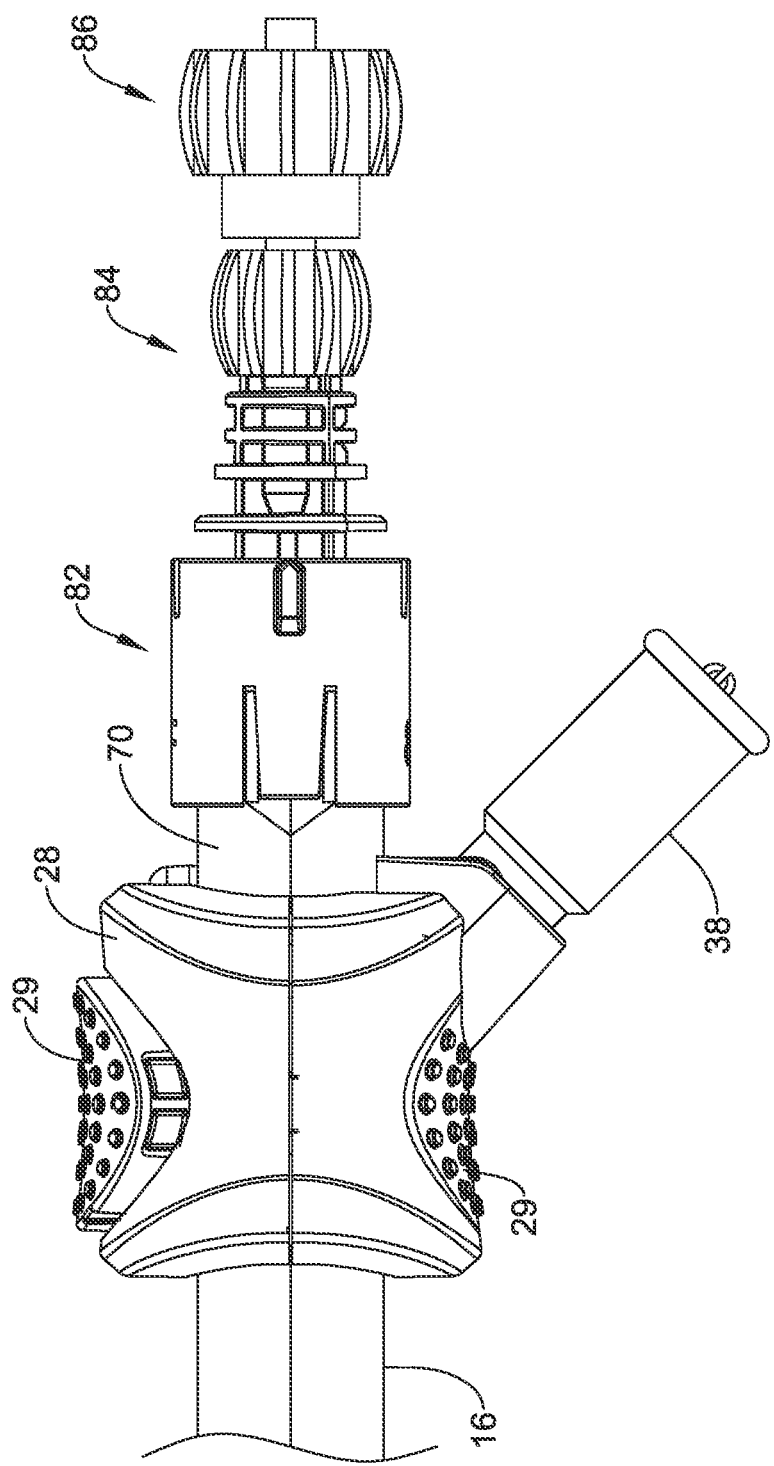
FIG. 8 is a side view of the illustrative delivery endcap assembly of FIG. 6A secured to the illustrative biliary access device of FIGS. 1A and 1B.

FIG. 7 is an exploded view, showing the delivery endcap assembly 80 disposed proximate the proximal end 70 of the handle 12 and FIG. 8 is a side view showing the delivery endcap assembly 80 secured to the proximal end 70 of the handle 12. It can be seen that the proximal end 70 of the handle 12 includes latching features 116 (e.g., tabs, ears, slots, recesses, etc.) that are adapted to engage the latches 80 formed as part of the delivery endcap 82. Accordingly, the delivery endcap assembly 80 may be easily secured relative to the proximal end 70 of the handle 12.

Figure 9:
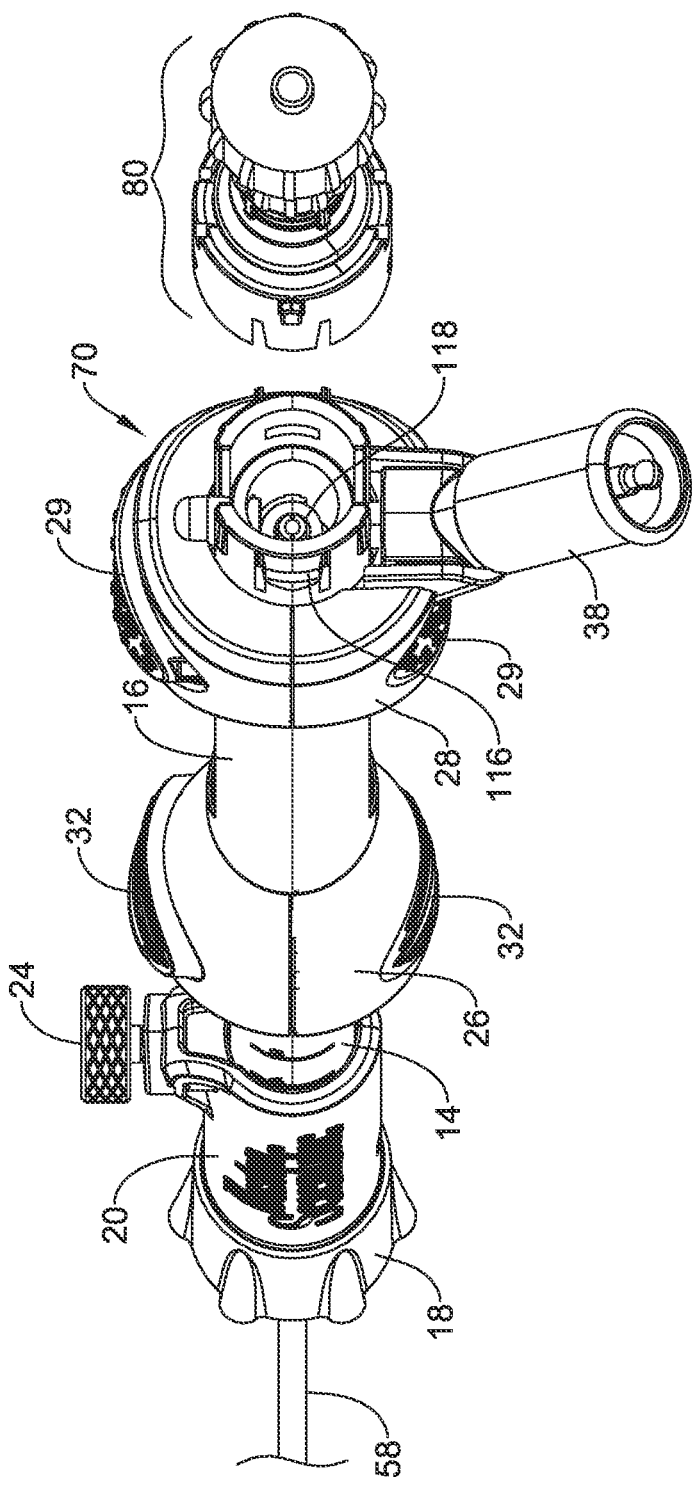
FIG. 9 is a perspective exploded view of the illustrative delivery endcap assembly of FIG. 6A in combination with the illustrative biliary access device of FIGS. 1A and 1B.

FIG. 9 is a perspective view of the biliary access device 10, ready to receive the delivery endcap assembly 80. With the sharp cap 42 and sharp stylet 46 removed, as well as the endcap 40, rotation hub 44 and access cannula 56 removed, the biliary access device 10 includes a lumen 118 visible at the proximal end of the biliary access device 10. It will be appreciated that the lumen 94 extending through the delivery endcap 82 may be adapted to butt up against the lumen 118 visible within the biliary access device 10, or otherwise be aligned with and in communication with the lumen 118. The lumen 118 may represent a proximal portion of the electrosurgical sheath 58, for example.

Figure 10:
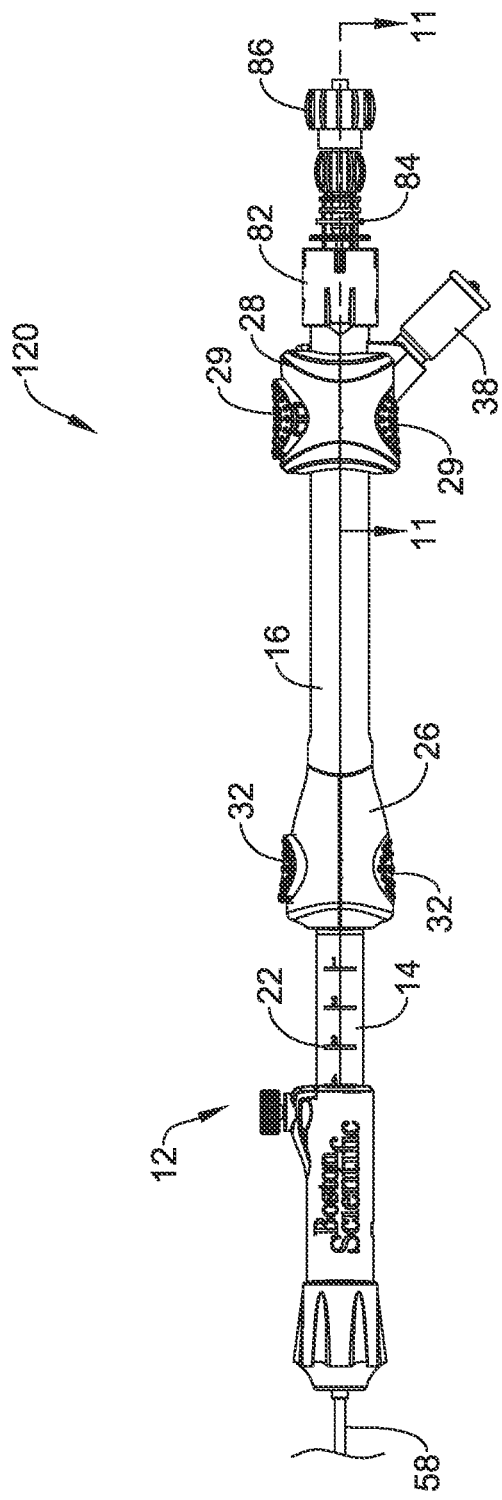
FIG. 10 is a side view of an illustrative assembly for deploying a medical device.

FIG. 10 is a side view of an illustrative assembly 120 that may be used for deploying a medical device within a desired treatment site. As an example, the illustrative assembly 120 may be adapted for deploying a medical device such as an expandable stent. In some cases, the illustrative assembly 120 may be adapted for deploying a medical device such as an expandable stent within a patient's biliary or pancreatic duct, or even within a pancreatic pseudocyst. In some cases, the assembly 120 may be considered as being an example of combining the biliary access device 10 (with certain components removed once access to the target anatomy has been gained) with the delivery endcap assembly 80.

Figure 11:
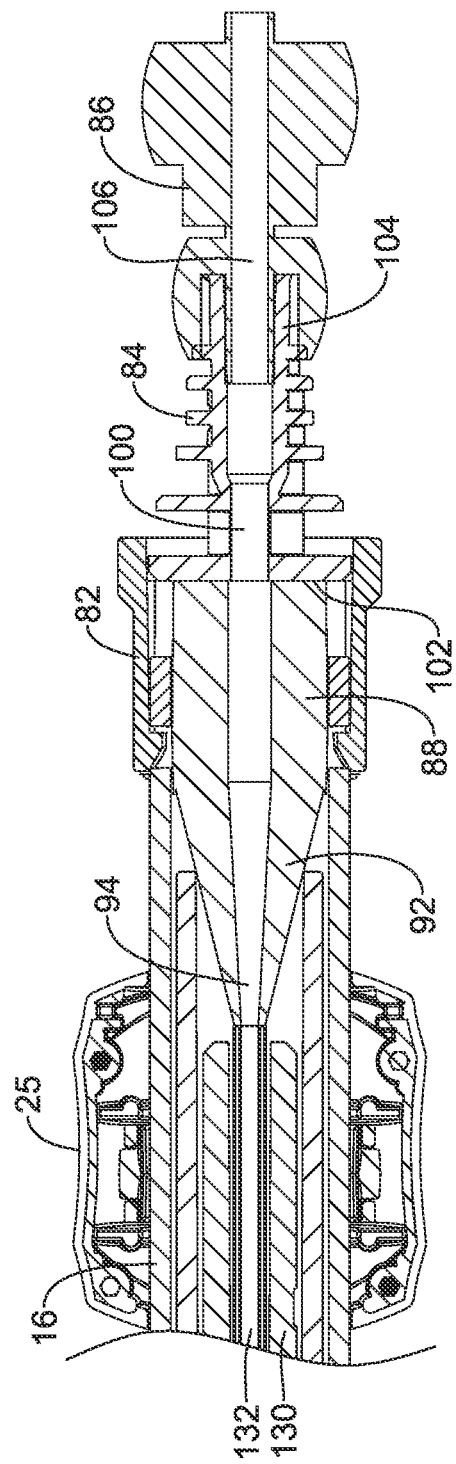
FIG. 11 is a cross-sectional view taken along line 10-10 of FIG. 10.

FIG. 11 is a cross-sectional view taken along the line 11-11 of FIG. 10. A sheath 132, which may for example represent the electrosurgical sheath 58 (or a separate sheath if present), axially aligns with the lumen 94 extending through the delivery endcap 82. The sheath 132 extends through a sled device 130 that functions to support the sheath 132 as it passes through the outer member 16. As can be seen, the lumen 94 extending through the delivery endcap 82 axially aligns with the lumen 100 extending through the delivery rotation hub 84 as well as the lumen 106 extending through the delivery valve 86. Any medical device that can fit through the lumens 58, 94, 100 and 106 can now be delivered through the assembly 120. While a variety of different medical devices are contemplated for delivery via the assembly 120, in some cases the assembly 120 may be considered as being adapted to deliver an expandable stent as the medical device.

Figure 12A:
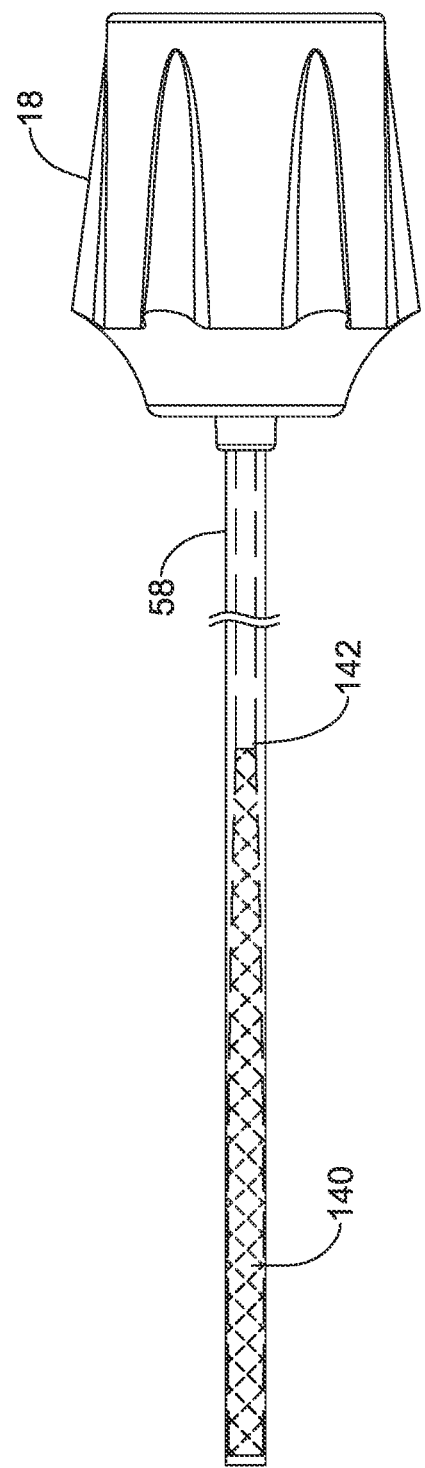
FIGS. 12A and 12B are side views showing an expandable stent being delivered through the illustrative assembly of FIG. 10.
Figure 12B:
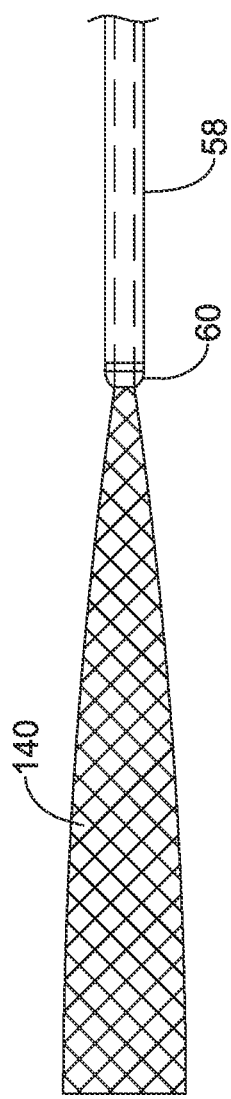

FIGS. 12A and 12B are side views showing an expandable stent being delivered through the illustrative assembly of FIG. 10. In FIG. 12A, an expandable stent 140 is shown being advanced through the electrosurgical sheath 130 that forms a part of the biliary access device 10 that, in combination with the delivery endcap assembly 80, forms the assembly 120. It will be appreciated that the electrosurgical sheath 130 is shown as being transparent in order to show the expandable stent 140. A mandrel 142 can be seen within the electrosurgical sheath 130, urging the expandable stent 140 distally. In FIG. 12B, the expandable stent 140 is beginning to emerge from the electrosurgical sheath 130, passing through the electrosurgical tip 60.

Figure 13:
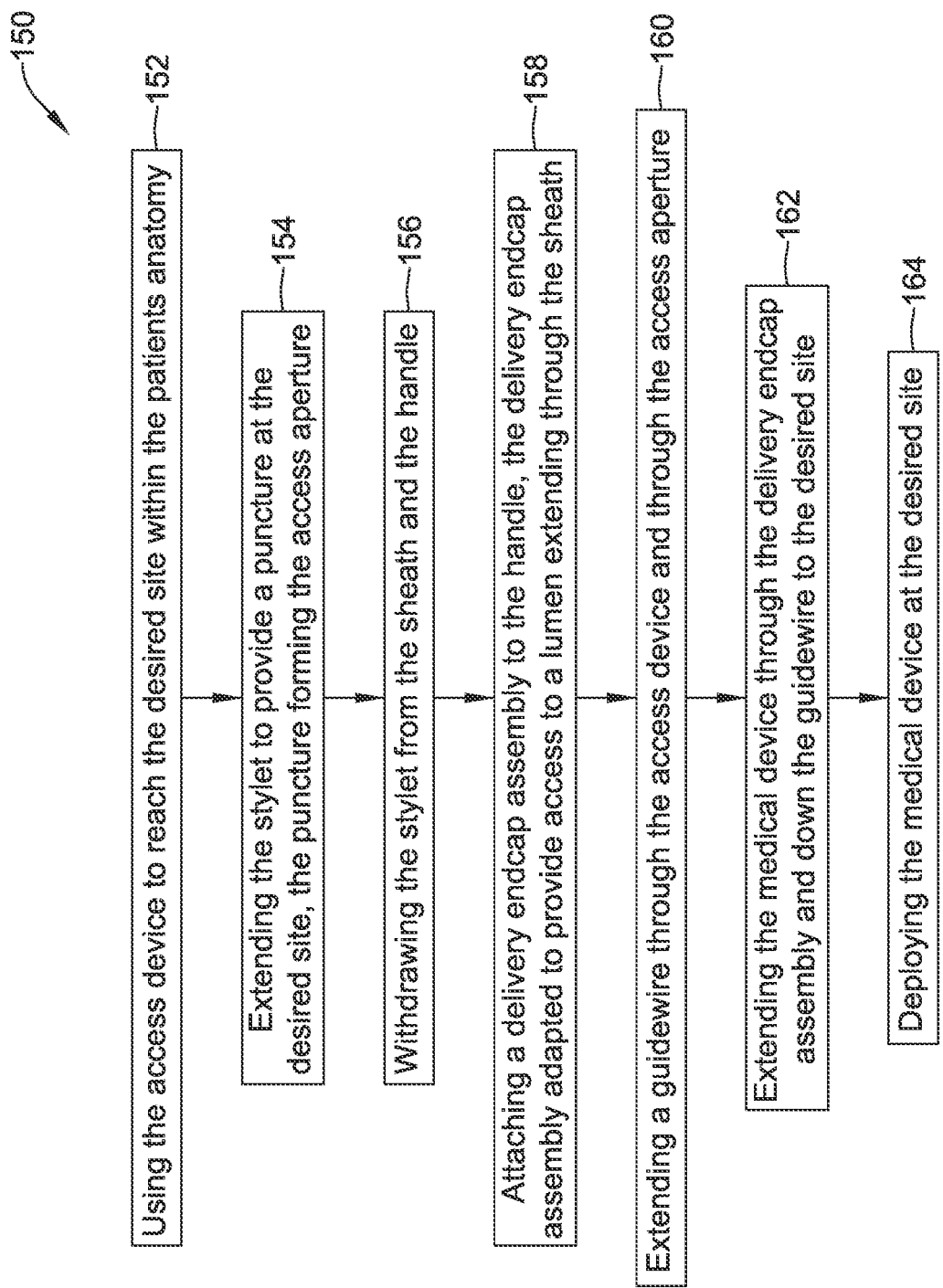
FIG. 13 is a flow diagram showing an illustrative method.

FIG. 13 is a flow diagram showing an illustrative method 150 of delivering a medical device using a biliary access device (such as the biliary access device 10) adapted to provide an access aperture providing access to a desired site within the patient's anatomy, the access device including a handle and a stylet distally extendable from the handle within a sheath. In some cases, the sheath includes an electrosurgical sheath with an electrosurgical tip disposed at a distal end of the electrosurgical sheath, and the method 150 further includes using the electrosurgical tip to enlarge the access aperture formed by the stylet.

The access device is used to reach the desired site within the patient's anatomy, as indicated at block 150. The stylet is extended to provide a puncture at the desired site, the puncture forming the access aperture, as indicated at block 154. The stylet is subsequently withdrawn from the sheath and the handle, as indicated at block 156. A delivery endcap assembly is attached to the handle, the delivery endcap assembly adapted to provide access to a lumen extending through the sheath, as indicated at block 158. A guidewire is extended through the access device and through the access aperture, as indicated at block 160. The medical device is extended through the delivery endcap assembly and down the guidewire to the desired site, as indicated at block 162. The medical device is deployed at the desired site, as indicated at block 164.

In some cases, the medical device to be delivered includes an expandable stent disposed within an introducer sheath, the introducer sheath adapted to butt up against a proximal end of the electrosurgical sheath such that a mandrel may be used to advance the expandable stent through the biliary access device. In some cases, the delivery endcap assembly includes a securement portion adapted to be releasably securable to a proximal end of the handle after the stylet has been removed from the handle, a tapered portion extending proximally from the securement portion, a rotation hub adapted to be coupled to the securement portion, a valve adapted to be coupled to the rotation hub, and a lumen extending through the delivery endcap assembly, where the lumen extending through the delivery endcap assembly is adapted to permit a medical device within an introducer sheath to be advanced through the biliary access device.

The devices described herein, including but not limited to the biliary access device 10, the delivery endcap assembly 80 and the assembly 120 may be formed of a variety of different materials. In some cases, the biliary access device 10, the delivery endcap assembly 80 and the assembly 120 may be formed of one or more polymeric materials. In some cases, the various components of the biliary access device 10, the delivery endcap assembly 80 and the assembly 120 may be formed of polymers such as polyurethane.

Additional examples of suitable polymers include but are not limited to polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, biocompatible polymers, other suitable materials, or mixtures, combinations, copolymers thereof, polymer/metal composites, and the like.

It should be understood that this disclosure is, in many respects, only illustrative. Changes may be made in details, particularly in matters of shape, size, and arrangement of steps without exceeding the scope of the disclosure. This may include, to the extent that it is appropriate, the use of any of the features of one example embodiment being used in other embodiments. The invention's scope is, of course, defined in the language in which the appended claims are expressed.

What is claimed is:

1. An assembly for deploying a medical device within a biliary or pancreatic duct of a patient, the assembly comprising:
    a biliary access device including:
        a handle;
        an electrosurgical sheath movable relative to the handle, the electrosurgical sheath including an electrosurgical tip and defining an electrosurgical sheath lumen extending through the electrosurgical sheath;
        an access cannula extendable through the electrosurgical sheath lumen, the access cannula defining a cannula lumen extending through the access cannula, the access cannula adapted to be removable from the biliary access device;
        a sharp stylet extendable through the cannula lumen, the sharp stylet adapted to be removable from the biliary access device; and
        an access endcap assembly disposable at a proximal end of the handle, the access endcap assembly adapted to be removable from the biliary access device; and
    a delivery endcap assembly adapted to be securable to the proximal end of the handle in place of the access endcap assembly, the delivery endcap assembly including:
        a securement portion adapted to be releasably securable to the proximal end of the handle; and
        a lumen extending through the delivery endcap assembly and adapted to accommodate the medical device therethrough.

2. The assembly of claim 1, wherein the delivery endcap assembly further includes:
    a tapered portion extending proximally from the securement portion;
    a rotation hub adapted to be coupled to the securement portion; and
    a valve adapted to be coupled to the rotation hub;
    wherein the lumen of the delivery endcap assembly extends through each of the tapered portion, the rotation hub and the valve.

3. The assembly of claim 1, wherein the access endcap assembly further comprises a rotation hub.

4. The assembly of claim 3, wherein the sharp stylet further comprises a sharp cap that is adapted to releasably secure the sharp stylet to the rotation hub.

5. The assembly of claim 3, wherein the access cannula is operably coupled with the rotation hub such that rotation of the rotation hub causes rotation of the access cannula.

6. The assembly of claim 3, wherein the access cannula is operably coupled with the rotation hub such that removal of the rotation hub also removes the access cannula from the biliary access device.

7. The assembly of claim 1, wherein the lumen of the delivery endcap assembly is positionable in alignment with and in communication with the electrosurgical sheath lumen such that the electrosurgical sheath is adapted to accommodate the medical device extending through the electrosurgical sheath lumen once the access cannula and the sharp stylet have been removed from the biliary access device and the delivery endcap assembly has been secured to the proximal end of the handle of the biliary access device.

8. The assembly of claim 1, wherein the medical device comprises an expandable stent disposed within an introducer sheath.

9. The assembly of claim 8, wherein the introducer sheath is adapted to engage a proximal end of the electrosurgical sheath lumen such that a mandrel may be used to advance the expandable stent from the introducer sheath through the electrosurgical sheath lumen.

10. The assembly of claim 1, wherein the handle comprises an inner member and an outer member, the inner member slidingly disposed within the outer member;
    wherein translating the inner member relative to the outer member causes the sharp stylet to translate.

11. The assembly of claim 10, wherein the handle further comprises an electrosurgical actuator slidingly coupled with the outer member of the handle;
    wherein translating the electrosurgical actuator relative to the handle causes the electrosurgical sheath to translate.

12. The assembly of claim 1, wherein the delivery endcap assembly further comprises a modified rotation hub.

13. A delivery endcap assembly adapted for use with a biliary access device that is adapted for providing access to a treatment site, the biliary access device including a handle, a sheath extending proximally from the handle and one or more removable components extending proximally within the sheath, the one or more removable components adapted for providing access, the delivery endcap assembly adapted to permit a medical device to be delivered through the biliary access device, the delivery endcap assembly comprising:
- a securement portion adapted to be releasably securable to a proximal end of the handle after the one or more removable components have been removed from the handle;
- a tapered portion extending proximally from the securement portion;
- a rotation hub adapted to be coupled to the securement portion;
- a valve adapted to be coupled to the rotation hub; and
- a lumen extending through the delivery endcap assembly;
- wherein the lumen extending through the delivery endcap assembly is adapted to permit a medical device within an introducer sheath to be advanced through the biliary access device.

14. The delivery endcap of claim 13, wherein one of the one or more removable components comprises a sharp stylet operably coupled with a sharp stylet cap removably securable to the biliary access device.

15. The delivery endcap of claim 14, wherein one of the one or more removable components comprises an access cannula operably coupled with a rotation hub removably securable to the biliary access device.

16. The delivery endcap of claim 14, wherein the medical device comprises an expandable stent disposed within an introducer sheath, the introducer sheath adapted to butt up against a proximal end of the sheath such that a mandrel may be used to advance the expandable stent through the biliary access device.

* * * * *